United States Patent
Sittinger et al.

(10) Patent No.: US 9,125,871 B2
(45) Date of Patent: *Sep. 8, 2015

(54) CELL-FREE GRAFT

(75) Inventors: Michael Sittinger, Berlin (DE); Eszter Tánczos, Kuesnacht (CH); Christian Kaps, Berlin (DE)

(73) Assignee: BioTissue AG, Zurich (CH)

(*) Notice: Subject to any disclaimer, the term of this patent is extended or adjusted under 35 U.S.C. 154(b) by 1266 days.

This patent is subject to a terminal disclaimer.

(21) Appl. No.: 11/994,114
(22) PCT Filed: Jun. 29, 2006
(86) PCT No.: PCT/EP2006/006281
§ 371 (c)(1), (2), (4) Date: Dec. 27, 2007
(87) PCT Pub. No.: WO2007/003324
PCT Pub. Date: Jan. 11, 2007

(65) Prior Publication Data
US 2008/0206302 A1 Aug. 28, 2008

(30) Foreign Application Priority Data
Jun. 30, 2005 (DE) .......... 10 2005 030 614

(51) Int. Cl.
A61F 13/00 (2006.01)
A61F 2/50 (2006.01)
(Continued)

(52) U.S. Cl.
CPC .......... *A61K 35/16* (2013.01); *A61L 27/34* (2013.01); *A61L 27/3616* (2013.01); *A61L 27/50* (2013.01);
(Continued)

(58) Field of Classification Search
CPC .......... A61L 27/00; A61L 27/14–27/26; A61L 27/34; A61L 27/50; A61L 27/52; A61L 27/54; A61L 27/56; A61L 27/58; A61K 35/16; A61K 38/00; A61K 38/16; A61K 38/18; A61K 38/19; A61K 38/21; A61K 38/22
See application file for complete search history.

(56) References Cited

U.S. PATENT DOCUMENTS

| 4,582,865 A | 4/1986 | Balazs et al. |
| 4,813,967 A | 3/1989 | Renard et al. |

(Continued)

FOREIGN PATENT DOCUMENTS

| CA | 2629794 A1 | 5/2007 |
| DE | 19957388 A1 | 0/6200 |

(Continued)

OTHER PUBLICATIONS

Japanese Office Action, issued Feb. 15, 2011, for related Application No. JP 2008103337 (5 pages).

(Continued)

*Primary Examiner* — Lakshmi Channavajjala
(74) *Attorney, Agent, or Firm* — McGlinchey Stafford, PLLC; R. Andrew Patty, II

(57) ABSTRACT

The invention proposes a cell-free graft, comprising (i) a cohesive, structure-forming matrix with open porosity made from a biologically and pharmaceutically acceptable material and (ii) serum.
In one particularly preferred embodiment, the matrix additionally contains a gel.
By virtue of a second aspect, a method of producing such a cell-free graft is proposed, whereby the matrix and the gel, if one is provided, is placed in contact with the serum. The graft may optionally be dried with serum. Alternatively, the matrix and the gel, if one is provided, are in the dried state before being placed in contact with the serum.
By virtue of a third aspect, finally, the invention proposes the use of the cell-free graft for regenerating tissue and in particular for regenerating cartilage and/or bone.

38 Claims, 2 Drawing Sheets

(51) Int. Cl.
| | |
|---|---|
| *A61L 27/52* | (2006.01) |
| *A61L 27/54* | (2006.01) |
| *A61L 27/56* | (2006.01) |
| *A61K 39/395* | (2006.01) |
| *A61K 35/16* | (2015.01) |
| *A61L 27/34* | (2006.01) |
| *A61L 27/36* | (2006.01) |
| *A61L 27/50* | (2006.01) |
| *A61K 38/00* | (2006.01) |

(52) U.S. Cl.
CPC ............... *A61L 27/52* (2013.01); *A61L 27/54* (2013.01); *A61L 27/56* (2013.01); *A61K 38/00* (2013.01); *A61L 2300/414* (2013.01); *A61L 2430/02* (2013.01); *A61L 2430/06* (2013.01)

(56) References Cited

U.S. PATENT DOCUMENTS

| | | | |
|---|---|---|---|
| 4,828,563 | A | 5/1989 | Müller-Lierheim |
| 5,891,455 | A | 4/1999 | Sittinger et al. |
| 5,932,459 | A | 8/1999 | Sittinger et al. |
| 6,506,217 | B1 | 1/2003 | Arnett |
| 6,602,294 | B1 * | 8/2003 | Sittinger et al. ........... 623/23.63 |
| 6,872,819 | B1 | 3/2005 | Pavesio et al. |
| 2002/0052044 | A1 | 5/2002 | Jeschke et al. |
| 2002/0119179 | A1 | 8/2002 | Rezania et al. |
| 2003/0003153 | A1 | 1/2003 | Asculai et al. |
| 2003/0031695 | A1 | 2/2003 | Kadiyala et al. |
| 2004/0076656 | A1 | 4/2004 | Pavesio et al. |
| 2004/0241144 | A1 | 12/2004 | Kaps et al. |
| 2004/0267362 | A1 * | 12/2004 | Hwang et al. .............. 623/13.15 |
| 2005/0043814 | A1 * | 2/2005 | Kusanagi et al. .......... 623/23.58 |
| 2005/0147642 | A1 | 7/2005 | Laredo et al. |
| 2005/0283224 | A1 | 12/2005 | King |
| 2006/0241756 | A1 | 10/2006 | Fritz et al. |
| 2007/0020230 | A1 | 1/2007 | Kaps et al. |
| 2008/0206302 | A1 | 8/2008 | Sittinger et al. |
| 2008/0260801 | A1 | 10/2008 | Ahlers et al. |
| 2009/0017093 | A1 | 1/2009 | Springer et al. |

FOREIGN PATENT DOCUMENTS

| | | |
|---|---|---|
| DE | 4306661 A1 | 9/1994 |
| DE | 4431598 A1 | 3/1996 |
| DE | 10006822 A1 | 8/2001 |
| DE | 10042484 A1 | 3/2002 |
| DE | 1139783 C1 | 4/2003 |
| DE | 10333901 A1 | 3/2005 |
| DE | 10348219 A1 | 5/2005 |
| DE | 102005034420 A1 | 7/2006 |
| DE | 102005054940 A1 | 5/2007 |
| EP | 1273312 A2 | 1/2003 |
| EP | 1410811 A1 | 4/2004 |
| GB | 1052589 * | 12/1966 |
| GB | 1052589 A | 12/1966 |
| JP | 61502448 | 10/1986 |
| JP | 62049856 | 3/1987 |
| WO | WO 94/14390 | 7/1994 |
| WO | 9715655 A2 | 5/1997 |
| WO | WO 01/54735 A2 | 8/2001 |
| WO | 0166130 A1 | 9/2001 |
| WO | 0200272 A2 | 1/2002 |
| WO | 0238163 A1 | 5/2002 |
| WO | WO 02/067762 A2 | 9/2002 |
| WO | WO 02/083878 A1 | 10/2002 |
| WO | WO 2005014027 A1 | 2/2005 |
| WO | WO 2006/104901 A2 | 10/2006 |

OTHER PUBLICATIONS

Hooiveld, M. J. J., et al., "Haemoglobin-derived iron-dependent hydroxyl radical formation in blood-induced joint damage: an in vitro study", Rhuematology 2003, vol. 42, p. 784-790 (7 pages).

Hooiveld, Michel J. J., et al., "Immature Articular Cartilage is More Susceptible to Blood-Induced Damage Than Mature Articular Cartilage", Arthritis & Rheumatism, Feb. 2003, vol. 48, No. 2, p. 396-403 (8 pages).

Shu, Xiao Zheng, et al., "In situ crosslinkable hyaluronan hydrogels for tissue engineering", Biomaterials 25, 2004, p. 1339-1348 (10 pages).

Lee, Sang young, et al., "In vivo conjunctival reconstruction using modified PLGA grafts for decreased scar formation and contraction", Biomaterials 24 (2003) pp. 5049-5059 (11 pages).

Liu, Haifeng, et al., "Construction of Chitosan-Gelatin-Hyaluronic Acid Artifical Skin in Vitro", Journal of Biomaterials Applications, vol. 21, Apr. 2007, pp. 413-430 (18 pages).

Shu, Xiao Zheng, et al., "Disulfide-crosslinked hyaluronan-gelatin hydrogel films: a covalent mimic of the extracellular matrix for in vitro cell growth", Biomaterials 24 (2003) pp. 3825-3834 (10 pages).

* cited by examiner

CELL-FREE GRAFT

REFERENCE TO RELATED APPLICATIONS

This application is a 371 national phase of PCT Application PCT/EP2004/006281, filed Jun. 29, 2006, the text of which is not in English, which PCT Application claims the priority of German Application No. 10 2005 030 614.4-43, filed Jun. 30, 2005, the text of which is not in English.

This invention relates to a cell-free graft for regenerating tissue and in particular for regenerating cartilage, a method of producing same and the use of the graft for regenerating tissue.

BACKGROUND OF THE INVENTION

Cartilage is a form of mesodermal tissue derived from the connective tissue, which is created by multi-potent, undifferentiated, mesenchymal precursor cells. A distinction is made between three types of cartilage, hyaline, elastic and fibrocartilage. Hyaline cartilage is by far the most common form of cartilage and is found in the joint surfaces, for example. Cartilage defects caused by wear or damage are a widespread medical problem. Due to the denseness of the cartilage of the body's conventional inflammation and repair system, it has only a low capacity for self-healing. This being the case, methods and techniques have been developed in the past, and in particular over the last few years, as a means of replacing chondral as well as osteochondral areas in the joint cartilage. For example, joint cartilage has been replaced by perios, perichondrium, allogenic and autologous osteochondral grafts, allogenic meniscuses or prostheses made from synthetic materials.

In situations involving autologous grafting of chondrocytes, chondrocytes taken from the patient are grown in cell culture and given back to the patient again. They may be given back in the form of various different types of transplants. Examples of these are injection solutions which are injected into the joint, matrices injected with cartilaginous cells and similar.

Patent specification WO 97/15655, for example, describes artificial tissue comprising three-dimensional extra-cellular matrices and genetically manipulated cells, and the matrices are able to release immunosuppressive or cell-differentiating factors. These matrices preferably take the form of a polymer fleece, through which a cell suspension, which may be suspended in a fibrinogen solution, is distributed. Factors or components of the corresponding extra-cellular matrix which are necessary for the growth and/or differentiation process may also be added to the matrix. In order keep the cells in the matrix, the cell suspensions may be solidified by adding thrombin, thereby resulting in the finished graft.

Patent specification DE 44 31 598 describes a method of producing an implant of cell cultures, whereby three-dimensional support structures to which the cells are applied are firstly encapsulated and then perfused with a nutrient solution. Resorbable micro-bodies are incorporated in the support structures, which release factors influencing tissue formation as they are resorbed.

Patent specification DE 43 06 661 describes a three dimensional support structure, preferably made from a polymer fleece, in which the cells are incorporated. The support structure is then perfused with nutrient solution in order to promote cell growth and the formation of an extracellular matrix by the cells. In order to prevent the cells from migrating or draining out, the support structure is encapsulated with agarose.

Patent specification DE 101 39 783 also discloses the use of mesenchymal cells in synovial fluid. If desired, this composition can also be applied to a support, such as a fleece or a plastic, and used as a graft in this form. Otherwise, the suspension of cells in synovial fluid is injected as such into the relevant joint.

Alternatively, matrix structures are synthesized which do not actually contain any cells. For example, patent specification US 2003/0003153 describes stiffened matrix membranes containing one or more structure-forming proteins suitable for cell growth. Suitable proteins are collagen, for example. The resultant matrices in membrane form may be injected with cells or grafted as they are. In the latter case, it is assumed that cells from the body's own tissue will migrate into the matrix structure. It is done by means of a conventional Pridie puncture or micro-fracturing, for example. With these techniques, small punctures or fractures are made in the joint bone as far as the bone marrow. Blood flows through the punctures into the defect, as a result of which the defect is filled with a blood graft. The graft contains mesenchymal precursor cells, which, stimulated by appropriate impetuses, are able to form a cartilage-type replacement tissue, the so-called fibrocartilage. If a matrix material is placed over the Pridie puncture, the blood cells are able to migrate into this matrix material, where they then become established.

Patent specifications DE 199 57 388 and WO 2005/014027 use this effect and enhance it by incorporating growth and differentiating factors (DE 199 57 388) or chemokines (WO 2005/014027) in the matrix structure as recruiting means. All the factors are intended to result in enhanced recruitment of cartilage-forming mesenchymal precursor cells, the ultimate aim being to regenerate the cartilage more rapidly.

Patent specification WO 02/00272, finally, discloses the possibility of producing appropriate grafts from blood and a polymer component. The underlying problem addressed by this document is the fact that the blood graft which forms as standard using the Pridie puncture technique contracts on coagulation and thus changes shape. The added polymer prevents this change of shape and thus permits healing true to shape. In order to produce the graft, a polymer is mixed with blood or a blood component such as erythrocytes, leukocytes, monocytes, platelets, fibrinogen, thrombin and platelet-rich plasma and introduced into the defect. If using a blood component, however, the presence of material capable of coagulating is a significant factor in terms of achieving the desired effect.

Grafts made from chitosan and chondrocytes may be used as an alternative. Since the cells are introduced into the defect as described above, the addition of substances for attraction purposes and/or growth and differentiating factors can be dispensed with.

The technologies described above have disadvantages because if the graft itself contains cells, they are often damaged due to manipulation during handling, and if cells are used for the graft, in particular autologous cells, they have to be produced by a lengthy culture process and have to be carefully controlled to prevent contamination, and finally, there is no possibility of storage. In parallel, the recruitment of cell-free grafts of mesenchymal cells through a Pridie puncture, with or without substances used for attraction purposes, has proved unsatisfactory. Colonization is slow, is initiated by few cells and is also non-specific. This means that different cell types are flushed into the graft from the blood leaving the Pridie puncture and remain there. However, it is only colonization by mesenchymal precursor cells which differentiate to chondrocytes that is desired. In the case of conventional grafts, however, this is not guaranteed.

Amongst other things, therefore, the objective of the invention is to propose a graft which is simple to produce, can be readily stored and is simple to apply. Furthermore, it would be desirable to increase recruitment rates by means of the graft, obtain better selectivity for the type of cells recruited and disposed in the graft, and to dispense as far as possible with the use of growth factors foreign to the body and optionally even recombinant growth factors, which represent potential allergens.

SUMMARY OF THE INVENTION

The invention overcomes these and other problems known from the prior art. To this end, a cell-free graft is proposed, comprising (i) a cohesive, structure-forming matrix with an open porosity made from a biologically and pharmaceutically acceptable material and (ii) serum. In one particularly preferred embodiment, the matrix additionally contains a gel.

By virtue of a second aspect, a method of producing such a cell-free graft is proposed, whereby the matrix and the gel, if one is provided, are placed in contact with the serum. Optionally, the graft may be dried with serum. Alternatively, the matrix and the gel, if one is provided, may be in the dried state before being placed in contact with the serum.

Based on a third aspect, the invention finally relates to the use of the cell-free graft for regenerating tissue and in particular for regenerating cartilage and/or bone.

DETAILED DESCRIPTION OF THE INVENTION

Figure 1:
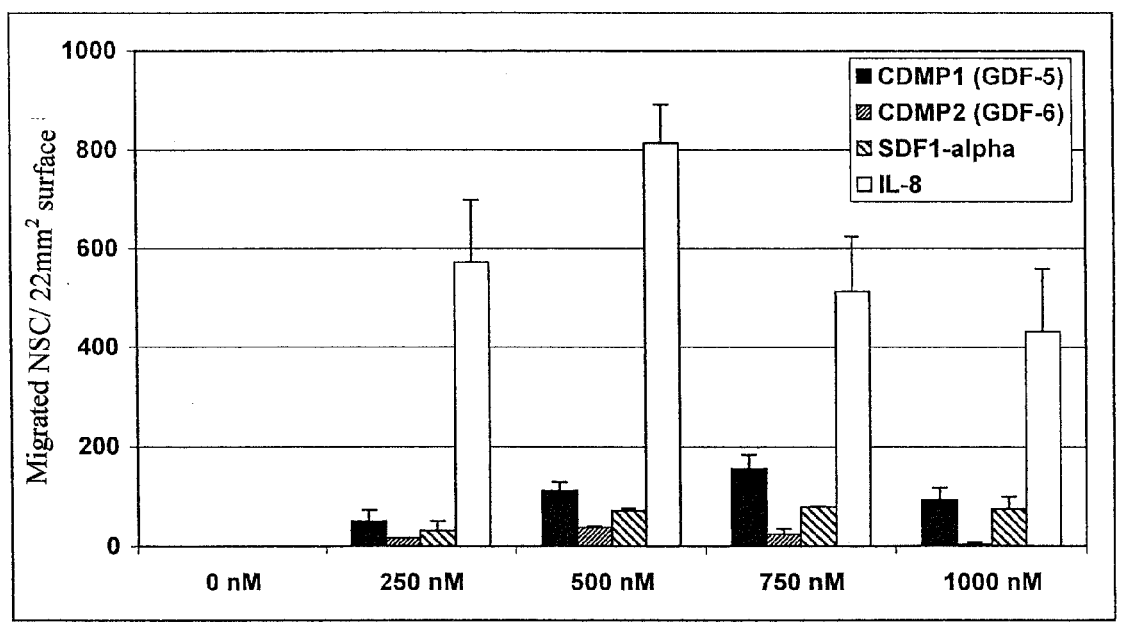
FIG. 1 shows the chemotactic effect of CDMP1, CDMP2, SDFI-α and IL8 on human mesenchymal stem cells in vitro.

As explained above, the invention relates to a cell-free graft, comprising (i) a cohesive, structure-forming matrix with open porosity made from a biologically and pharmaceutically acceptable material and (ii) serum. Surprisingly, using serum in the cell-free graft proposed by the invention enables the recruitment efficiency of mesenchymal precursor cells from the bone marrow through which blood flows to be increased by several factors. This surprising increase in recruitment efficiency in turn obviates the need to introduce differentiated cells or precursor cells into the graft separately, which facilitates and shortens handling of the graft and also permits storage.

Blood serum can be easily obtained in a conventional manner. By preference, it may be taken directly from the patient during the transplant. Autologous material can therefore be implanted in the patient, but there is no need to add other, potentially allergenic and/or immuno-active factors.

The matrix of the cell-free graft proposed by the invention is a cohesive, structure-forming matrix of open porosity. The expression "cohesive" in this context should be construed as meaning that the matrix enables the graft to be handled without falling apart into individual parts or bits. It is not necessary for all parts of the matrix to be bonded to one another by chemical bonds or interactions. A mechanical join in the form of weaving, fulling, twisting or similar is sufficient.

The expression "structure-forming" in this context should be construed as meaning the property of the matrix to function as a structure former for the cells migrating to the tissue matrix to be produced. The matrix also acts as a frame or lattice which the cells are able to colonize and where they find purchase, so that they are not entrained out of the matrix by synovial fluid or blood, for example.

Finally, "open porosity" in the context of the invention should be construed as meaning that the spaces between the frame structures of the matrix are accessible to a substance and in particular a fluid exchange with the area around the matrix. The pore size of the pores is preferably dimensioned so that penetration or circulation is also possible by cells. However, the expression open porosity as used in the context of the invention is also intended to mean a structure such as prevails in gels. It is here that the frame structures of the matrix are provided by the skeleton of the structure former. Disposed between them are hydrate pockets and fluid, which the cells can penetrate and which enable a fluid exchange. Appropriate gel structures should therefore also be construed as matrices with open porosity within the context of the invention.

The frame structures with open porosity are preferably selected from woven or non-woven fabrics (in particular fleece and felt structures), membranes, sponges, wadding, open-cell foams, wool, braids, ordered and random fiber bundles, porous ceramic materials, spongiosa and gels, as well as combinations of these. The matrix preferably has a fleece or felt structure. Combinations of different structures, for example in a layered arrangement, are also possible and fall within the scope of the invention.

In principle, the matrix material may be any appropriate, biologically and pharmaceutically acceptable material. The matrix material used in the matrix proposed by the invention may be resorbable or non-resorbable. Resorbable materials are preferred. The matrix is preferably a material selected from the group comprising natural and synthetic polymers, such as collagen, hyaluronic acid, chitosan, chitin, polysaccharides, celluloses and their derivatives, proteins, polypeptides, polyglycolic acid, poly-lactic acid, poly(glycolide, lactate), caprolactam, ceramic materials such as oxides, carbides, nitrides and carbonitrides of metals, in particular silicon oxide, titanium oxide and calcium oxide; minerals such as halogenides, in particular fluorides, hydroxides, sulfates of metals, preferably physiologically harmless metals such as calcium phosphate, appatite, hydroxyl appatite; metals such as titanium, aluminum, gold, silver, stainless steel and mixtures thereof. More specifically preferred are polyglycolic acid (PGA), polylactic acid, collagen or hyaluronic acid.

As regards polyglycolic acids, it is preferable to use pure polyglycolic acids with molecular weights of >20,000, preferably 30,000 to 70,000 g/mol, more especially preferably ca. 50,000 g/mol. The matrix material may be a fleece of polyglycolic acid, such as that sold by Alpha Research Switzerland GmbH under the trade mark PGA-Soft Felt7. In the case of this product, the resorption time in vivo is ca. 40 to 60 days. After seven days in vitro, the mechanical strength is still ca. 50% of the initial value as a result of hydrolysis.

In one particularly preferred embodiment, the cell-free graft also contains a gel in addition to the matrix. The gel is applied to at least one side of the matrix and/or at least partially penetrates it. By preference, the gel penetrates it fully. If the matrix contains such a gel, the matrix itself preferably has a different structure than that of a gel. More especially preferably, stiffer structures as explicitly specified above are used, with the exception of the gels. Accordingly, the gel is preferably of a lower stiffness than the matrix. Most preferably, fleece and felt structures are used, into which a gel is introduced.

The gel may be a natural or synthetic hydro-gel. It is preferably of a lower stiffness than the matrix. For example, the gel may be selected from polysaccharides, polypeptides, hyaluronic acid, fibrin, collagen, alginate, agarose and chitosan, as well as salts, derivatives and mixtures thereof. Suitable salts are alkali and earth alkali salts of said gels, for example. Most preferred are hyaluronic acid or a hyaluronic acid salt such as Na hyaluronate.

In terms of hyaluronic acid qualities, qualities produced by fermentation may be used. Alternatively, it is also possible to use hyaluronic acid obtained from animals. The mean molecular weight of the qualities used is generally between 250 and 6,000 kDa, preferably 1,000 to 2,000 kDa, most preferably approximately 1,200 kDa. Suitable hyaluronic acid products are commercially available. A suitable hyaluronic acid quality is TRB Chemedika AG sold under the Ostenil® trade mark, for example. This material is EC certified and therefore suitable for pharmaceutical purposes.

The gels may be obtained from sources, precipitation or polymerization of an appropriate gel former in a physiologically suitable solution. Examples of such suitable solutions are water such as aqueous solutions of salts (e.g. alkali and earth alkali halogenide (Cl, Br, I), carbonates, phosphates, citrates, acetates and similar), organic acids, buffer substances and mixtures thereof. Alternatively, more complex solutions may be used, such as culture media or body fluids or solutions derived from them such as synovial fluid or serum. The quantity of gel former used is selected so that an adequate viscosity of the gel is obtained. In the case of hyaluronic acid, this is usually within the range of 0.5-50 mg/ml, preferably 0.5-20 mg/ml, most preferably 10 mg/ml.

The most preferred graft is one with a matrix made from PGA fleece or felt, in which a hyaluronic acid gel is incorporated.

The dimensions of the cell-free graft proposed by the invention generally depend on the dimensions of the defect to be treated and the requisite size of the graft. The dimensions may be adapted as required by the doctor administering the treatment. For lesions in cartilage tissue, especially in the knee joint, these dimensions are usually in the range of 10 to 50 mm in length, 10 to 50 mm in width and 0.5 to 3 mm in thickness, preferably 10 to 30 mm in length, 10 to 30 mm in width and 1 to 2 mm in thickness. Most preferable would be sizes of 20×20 mm width and length and 1.1 to 2 mm thickness. Dimensions can be adapted for non-square shapes, e.g. rectangular, round, oval, polyhedral, etc.

The advantage of the combination of matrix and gel in the cell-free graft proposed by the invention is that the gel forms a mechanical barrier with respect to cells other than mesenchymal precursor cells of the blood penetrating the Pridie puncture or similar fractures. This enables a selective migration of mesenchymal precursor cells into the graft. Only these establish themselves in the matrix, therefore, and differentiate to the desired tissue cells. Other cells growing over the desired tissue-forming cells are therefore prevented or significantly reduced.

At the same time, the gel promotes the retention of the desired cells under mechanical stress before the natural biomatrix of the cartilage forms around the latter. This enables stress to be relieved earlier, once the patient has received the graft.

The second element needed for the cell-free graft proposed by the invention is serum, usually human serum. This may be autologous, allogenic or heterological. By serum for the purpose of the invention is meant the part of the blood which remains liquid once the blood has coagulated. Serum does not contain any blood cells and, unlike blood plasma, no fibrinogen. The other elements of blood plasma are also to be found in serum. These are fat, fatty acids, glycerin, sugar, salts, metals and plasma proteins. The plasma proteins include, for example, transport proteins, enzymes, proenzymes, enzyme inhibitors, the complement system, immuno-proteins, inflammation mediators and similar.

The serum to be used for the purpose of the invention may be modified by adding at least one element and/or removing at least one serum component. In a preferred embodiment, the serum is not modified. More especially preferred is an autologous serum. This can be obtained by taking blood from the patient and obtaining the serum using conventional methods. Obtained in this manner, the serum may be placed in contact with the matrix and with the gel, if one is provided, and thus incorporated in the graft, optionally by the doctor administering the treatment, directly at the site of the graft.

Alternatively, a modified serum is used. If the modification involves adding at least one constituent, it may be preferable to select the latter from the group comprising growth factors, differentiation factors (on this subject, see patent specification DE 199 57 388, which is incorporated herein by reference), hormones, cytokines, cellular adhesion molecules, chemotactic factors including chemokines, such as described in patent specification WO 2005/014027, which is incorporated herein by way of reference, enzymes, enzyme inhibitors, coenzymes, minerals, fats, lipids, saccharides, pharmaceutical substances such as antibiotics, analgesics, inflammation inhibitors and immuno-suppressants, buffer substances, stabilizers, in particular cryogenic stabilizers, and vitamins, preferably hormones, chemokines, growth factors and differentiation factors. The hormones, chemokines, growth and differentiation factors are preferably selected from insulin, PDGF, IGF, GMCSF, GDF5, GDF6, FGF, BMP2, BMP4, BMP7, IL8, SDF1-α and EGF. Most preferred is insulin. The matrix and/or the gel may also be modified by incorporating the elements listed above or mixtures thereof.

Alternatively, specific elements such as enzymes, immuno-proteins, proenzymes, sugars, etc., for example, may be selectively removed by means of affinity chromatography, for example. The serum may also be diluted. To this end, serum is mixed with the desired quantity of physiologically acceptable liquid, such as citrate buffer, PBS or similar.

The cell-free graft described above may be produced by a method whereby the matrix and, if one is provided, the gel, is placed in contact with the serum. This contacting may be done by applying in drops, softening, impregnation or soaking. By preference, if the gel is provided, it is incorporated in the matrix first of all and/or applied to it, after which the process of making contact with the serum takes place. If the cell-free graft contains other elements such as listed above, these may be incorporated in one or more of the matrix, gel and serum.

The method proposed by the invention may include a drying step. The advantage of using a drying step is that the graft can be stored for longer in dried form. If the matrix and, if one is provided, the gel, are dried before being placed in contact with the serum, this structure can be re-constituted by soaking or softening when placed in contact with serum, thereby transforming it into a ready-to-use state. Alternatively, if the structure comprising the matrix, gel, if one is provided, and serum is dried, it can be reconstituted by soaking or softening in serum or some other appropriate pharmaceutically and physiologically acceptable solution, as described above in connection with forming the gel, for example physiologically acceptable salt solution, and thus transformed into a ready-to-use state. If the graft proposed by the invention contains other elements, these may also be incorporated in the solution used to reconstitute the cell-free graft to the ready-to-use state. This may be desirable in particular if the other elements are proteins or non-stable co-factors.

In the case of the preferred embodiments made from polyglycolic acid fleece with hyaluronic acid gel described above, fleece sizes of 20 mm×20 mm×1.1 mm are used with ca. 400 µl of a hyaluronic acid solution (10 mg/ml) incorporated in the material in a physiologically suitable solution or already incorporated in serum. In the case of fleeces of 20 mm×20 mm×2 mm, ca. 730 µl of hyaluronic acid solution are used. If grafts of these dimensions are dried by lyophilization, for example, they can be reconstituted by soaking them in 1 to 2 ml of solution. In the case of dried matrices without serum, they are preferably reconstituted with serum or diluted serum, whereas dried matrices containing serum are preferably reconstituted in physiological salt solution.

Suitable serum concentrations are 1 to 100% by volume of the volume of gel and fluid contained in the matrix. Preferably, in the case of matrices without gel, serum concentrations of 10 to 100%, preferably 50 to 100% and most preferably 100% of the fluid volume are used, incorporated amongst other things by capillary forces. In order to reduce the serum concentration below 100%, serum diluted with physiologically acceptable salt solution may be used. In the case of matrices with gel, serum contents of 0.01 to 50% by volume, or stronger, preferably 0.5 to 20% by volume, and most preferably 1 to 10% by volume of serum may be used by reference to the total volume of gel, serum and optionally pharmaceutically acceptable liquid.

The cell-free graft proposed by the invention may be used to regenerate tissue and in particular to regenerate cartilage and/or bone. It is preferably used to regenerate mesenchymal tissue. Most preferably, it is used to regenerate cartilage and/or bone, in particular using the Pridie puncturing method or micro-fracturing. The graft acts as an intelligent cover which is introduced into the cartilage in an exact fit after Pridie puncturing or micro-fracturing in order to restore the joint surface. The matrix material, preferably felt material, imparts mechanical stability and acts as a conductive structure, which promotes the homogeneous, three-dimensional distribution of patients cells migrating in from the bone marrow and spongious bone. The gel, such as hyaluronic acid, acts as a barrier in order to prevent the inward migration of red blood cells and leukocytes. The serum, preferably autologous serum, promotes the migration of cells, especially mesenchymal precursor cells, into the graft and hence into the defect. Maturing or differentiation of the mesenchymal precursor cells which have migrated into the graft to form chondrocytes and hence build a cartilagenous regenerating tissue is induced by the hyaluronic acid, serum and the synovial fluid present in the joint. Surprisingly, using serum has been found to increase recruitment numbers significantly.

The examples given below are merely intended to illustrate the invention and should not be construed as restrictive it in any way.

EXAMPLE 1

Recruitment of Human Mesenchymal Stem Cells by Means of Growth and Differentiation Factors, Chemokines and Human Serum in Vitro A Isolation and Cultivation of Human Mesenchymal Stem Cells The way in which human mesenchymal stem cells (MSC) are isolated from bone marrow has already been described [DE 103 33 901]. A maximum of 3 ml of bone marrow punctate are mixed with 10 ml of PBS and centrifuged for 10 min. and at 310 g at room temperature. The cell pellet is re-suspended and washed with PBS again. The cells are placed in 20 ml of DME medium (with 10-20% FBS, 2% HEPES, 4 mM of L-glutamine, 100 U/ml of penicillin, 100 µg/ml of streptomycin). Every 5 ml of this cell suspension is introduced onto 20 ml of a Percoll density gradient with a density of 1.073 g/ml. The cells are centrifuged at 900 g for 32 min. The upper phase is transferred to a new centrifuge tube. This is centrifuged at 310 g for 6 minutes after adding 2.5-times the volume of PBS. The cell pellet is placed in DME medium. $1.5*10^5$-$3.5*10^5$ cells/cm$^2$ are transferred to culture in a cell culture flask and incubated at 37° C., 5% $CO_2$. The medium is changed for the first time after 72 hours, and then every 3-4 days. Isolated in this manner, the cells grow confluently after 2-3 weeks and are then transferred into a new culture vessel by means of trypsinization in a cell density of 6,000 cells/cm$^2$ culture surface (passage 1). After about one week, the cells are trypsinized again (passage 2). The homogeneity of this culture of human mesenchymal stem cells is verified by means of FACS analysis, in which connection the surface antigens endoglin and ALCAM are to be identified and the surface antigens CD34, CD 45 and CD 14 are not identified.

B Testing the Chemotactic Activity of Growth and Differentiation Factors (CDMP1, CDMP2) and Chemokines (SDF1-α, IL8) on Human Mesenchymal Stem Cells in Vitro The chemotactic effect of growth and differentiation factors, such as cartilage derived morphogenetic protein-1 CDNP1 or growth and differentiation factor-5, GDF5) and cartilage derived morphogenetic protein-2 (SDNP2 or growth and differentiation factor-6, GDF6) on mesenchymal stem and precursor cells has already been described [DE 199 57 388]. The chemotactic effect or use of chemokines, such as stromal derived factor-1α (SDF1-α) or interleukin-8 (IL8) for recruiting mesenchymal stem and precursor cells has also been described [DE 103 33 901].

Chemotactic activity is tested in so-called 96-well chemotaxis plates (ChemoTx system, Neuroprobe, USA). The test principle is based on transferring the substance to be tested, in solution, in a defined quantity and concentration to a well. The well is then covered by means of a membrane with pores (pore size in this instance 8 µm), so that the bottom face of the membrane is wetted by the solution containing the chemotactic solution.

A defined quantity of cell suspension which does not contain the substance to be tested is placed on the top face of the membrane remote from the well. After a few hours, a concentration gradient of substance to be tested develops, starting from the lower well through the membrane. If the substance to be tested is chemotactically active, cells of the cell suspension migrate through the pores of the membrane to the membrane bottom face and into the lower well. The migrated cells are dyed and their number is determined with the aid of a microscope.

For control purposes, lower wells are provided with the solvent of the substance to be tested, covered with the membrane and coated with the cell suspension. By microscopically counting the cells on the membrane bottom face (surface: 25 mm$^2$) and in the lower well, the cells which have migrated spontaneously due to the chemotactic substance without stimulus are determined. In order to determine the cell count recruited by the chemotactic substance, the number of spontaneously migrated cells is subtracted.

Prior to starting the test of the above-mentioned growth and differentiation factors and chemokines, human mesenchymal stem cells from bone marrow were displaced for 24 hours with diet medium (DME medium+1% of penicillin/streptomycin+0.5% of bovine serum albumin (BSA). The growth and differentiation factors and chemokines were placed in diet medium in different quantities to obtain defined solutions respectively of 250 nM, 500 nM, 750 nM and 1000 nM of the factors. 36 µl of the respective solutions were placed in triplicate in lower wells of the 96-well chemotaxis plate and covered with the membrane so that the membrane bottom face was wetted by the solutions. Diet medium was used as the control.

40 µl of diet medium with 30,000 human mesenchymal stem cells were placed on the top face of the membrane. After 20 hours of cultivation in the breeding cabinet at 37° C., 5% $CO_2$, the membrane was removed and placed in ice-cold ethanol/acetone (1:1 v/v) for 3 minutes in order to fix the cells. The membrane top face was thoroughly cleaned by means of a cotton bud to remove adhered cells. Cells on the membrane bottom face were dyed with Hemacolor solution (Merck, Darmstadt). No cells could be detected in the lower well.

The cells disposed on the bottom face of the membrane were counted by counting them under the microscope. The number of stem cells recruited by CDMP1, CDMP2, SDF1-α and IL8 in different concentrations was determined after subtracting the migrated cells in the control set (without chemotactic factor). The mean values of the cell counts with standard deviations are set out in FIG. 1 for the respective factors. CDMP1 was able to induce a maximum of 156 MSC (750 nM CDMP1) per 25 mm$^2$ to migrate. CDMP2 recruited a maximum of 38 MSC (500 nM CDMP2) per 25 mm$^2$, SDF1-α a maximum of 79 MSC (750 nM SDF1-α) per 25 mm$^2$ and IL8 a maximum of 814 MSC (500 nM IL8) per 25 mm$^2$.

Figure 2:
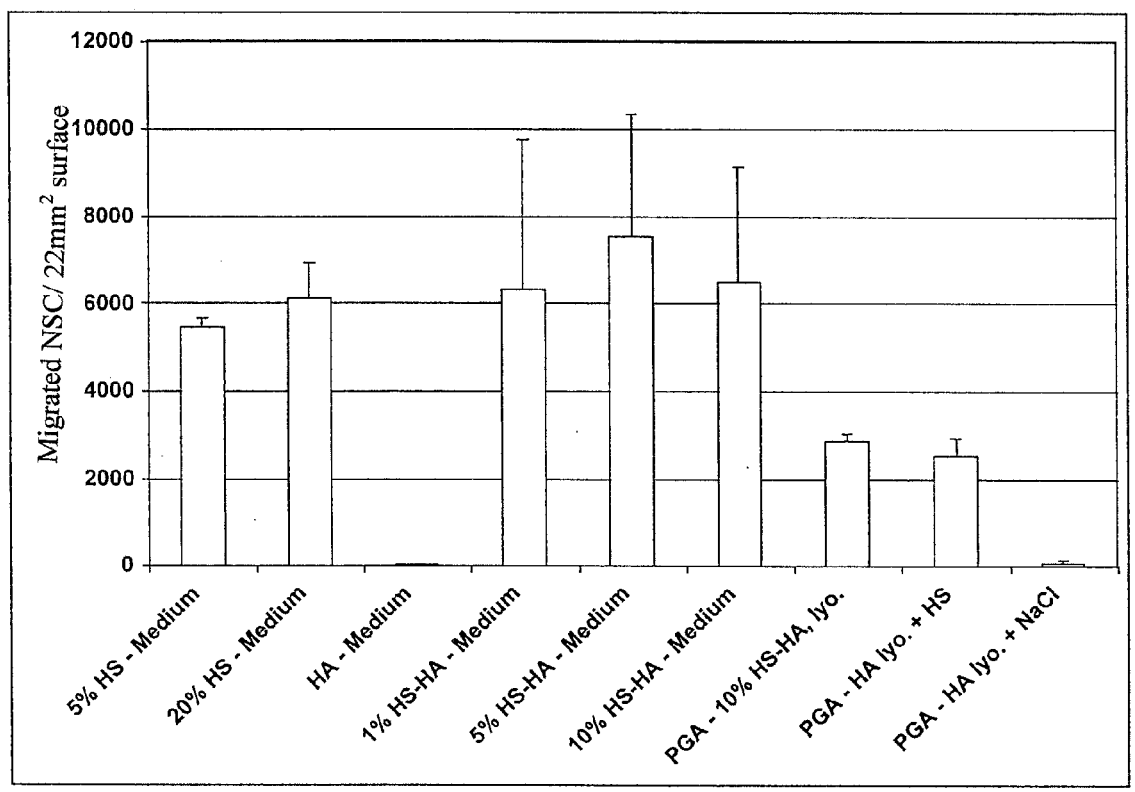
FIG. 2 shows the chemotactic effect of human serum of the blood on human mesenchymal stem cells in vitro.

C Testing the Chemotactic Activity of Human Serum of the Blood on Human Mesenchymal Stem Cells in Vitro Surprisingly, the testing of human serum by means of the test method described under B showed that human serum has a significantly stronger chemotactic effect on human mesenchymal stem and precursor cells in vitro than growth and differentiation factors and chemokines. The cell counts of the human mesenchymal stem and precursor cells recruited on average by human serum in different formulations (in diet medium or in hyaluronic acid) together with corresponding standard deviations are set out in FIG. 2. Depending on the formulation, a minimum 2,135 (PGA-HA lyo.+HS) and a maximum of 10,332 (5% HS-HA-medium) of human mesenchymal stem and precursor cells were recruited by human serum. Tests on hyaluronic acid without human serum in diet medium as a chemotactic factor showed on average 24 (HA medium) and on average 48 (PGA-Ha lyo.+NaCl) human mesenchymal stem and precursor cells which were recruited.

The following different formulations of human serum were used in the described test method to recruit human mesenchymal stem and precursor cells. Human serum was obtained from full blood samples (n=5) without anti-coagulants based on natural coagulation, mixed in equal parts and used to produce the different serum formulations. In order to produce the test sets "5% HS medium" and "10% HS medium", diet medium was displaced with human serum, resulting in 5% and 10% solutions. The "HA medium" test set comprises diet medium and hyaluronic acid obtained by fermentation (Ostenil®, TRB Chemedica AG) with a mean molecular weight of 1,200 kDa in equal parts. The "1% HS-HA medium", "5% HS-HA medium" and "20% HS-HA medium" test sets contain "HA medium" to which human serum was added, resulting in 1%, 5% and 10%-strength solutions.

In order to obtain the "PGA-10% Hs-HA, lyo." test set, 270 µl of hyaluronic acid obtained by fermentation (Ostenil®, TRB Chemedica AG) were mixed with 30 µl of human serum and applied to a fleece (PGA-Soft Felt®, Alpha Research Switzerland GmbH) comprising polyglycolic acid (PGA) with dimensions of 20 mm×15 mm×1.1 mm. The fleece soaked with the hyaluronic acid-serum mixture was frozen for 1 hour at −20° C. and then freeze-dried for 16 hours in the lyophilizer. To reconstitute it, the freeze-dried fleece was placed in 1 ml of physiological salt solution for 10 minutes, in order to obtain approximately 80-100 µl of the hyaluronic acid-serum solution by means of centrifugation for 10 minutes at 2,000 rpm. By diluting the solution with diet medium in equal parts, the formulation "PGA-10% HS-HA, lyo." was produced and used directly for testing chemotactic activity.

In order to make up the "PGA-Ha, lyo.+HS" test set, 300 µl of hyaluronic acid obtained by fermentation (Ostenil®, TRB Chemedica AG) were applied to a fleece (PGA-Soft Felt®, Alpha Research Switzerland GmbH) comprising polyglycolic acid (PGA) with dimensions of 20 mm×15 mm×1.1 mm. The fleece soaked with the hyaluronic acid was frozen for 1 hour at −20° C. and then freeze-dried for 16 hours in the lyophilizer. To reconstitute it, the freeze-dried fleece was placed in 1 ml of human serum for 10 minutes, in order to obtain approximately 80-100 µl of the hyaluronic acid-serum solution by means of centrifugation for 10 minutes at 2,000 rpm. By diluting the solution with diet medium in equal parts, the formulation "PGA-HA, lyo.+HS" was produced and used directly for testing chemotactic activity.

In order to make up the "PGA-Ha, lyo.+NaCl" test set, 300 µl of hyaluronic acid obtained by fermentation (Ostenil®, TRB Chemedica AG) were applied to a fleece (PGA-Soft Felt®, Alpha Research Switzerland GmbH) comprising polyglycolic acid (PGA) with dimensions of 20 mm×15 mm×1.1 mm. The fleece soaked with the hyaluronic acid was frozen for 1 hour at −20° C. and then freeze-dried for 16 hours in the lyophilizer. To reconstitute it, the freeze-dried fleece was placed in 1 ml of physiological salt solution for 10 minutes, in order to obtain approximately 80-100 µl of the hyaluronic acid solution by means of centrifugation for 10 minutes at 2,000 rpm. By diluting the solution with diet medium in equal parts, the formulation "PGA-HA, lyo.+NaCl" was produced and used directly for testing chemotactic activity.

EXAMPLE OF EMBODIMENT 2

A polyglycolic acid fleece commercially available under the trade mark PDA-Soft Felt® sold by Alpha Research Switzerland GmbH was cut to the dimensions of 20 mm×15 mm×1.1 mm. The material was impregnated with a hyaluronic acid mixture containing 10% serum as described in example 1 and then dried. Drying initially took place at −20° C. and then for 16 hours in the lyophilizer. The fleece was reconstituted by soaking with 1 to 2 ml of physiological salt solution for 10 min.

In an alternative test set, the fleece was impregnated with pure hyaluronic acid, 10 mg/ml dissolved in physiological salt solution. Prepared in this manner, the material was dried as described above. It was reconstituted by soaking it in 1 to 2 ml of serum for 10 min. Both fleeces may be used directly for grafting.

The invention claimed is:

1. A cell-free graft comprising (i) a cohesive, structure-forming matrix with open porosity made from a biologically and pharmaceutically acceptable material structure selected from fleece or felt structures, wadding, wool, and any combinations thereof and (ii) human serum in a concentration in the range of about 0.01% to 50% by volume, and (iii) a gel which is applied to at least one side of the matrix and at least partially penetrates it, which gel is selected from polysaccharides, hyaluronic acid, alginate, agarose and chitosan, as well as mixtures thereof.

2. Cell-free graft according to claim 1, wherein the matrix material is resorbable or non-resorbable.

3. Cell-free graft according to any one of claims 1-2, wherein the matrix comprises a material selected from the group consisting of natural and synthetic polymers, ceramic materials, minerals, metals and mixtures thereof.

4. Cell-free graft according to claim 1, wherein the gel is a natural or synthetic hydro-gel.

5. Cell-free graft according to claim 4, wherein the gel is of a lower stiffness than the matrix.

6. Cell-free graft according to claim 1, wherein the gel is of a lower stiffness than the matrix.

7. Cell free graft according to claim 1, wherein the gel comprises hyaluronic acid.

8. Cell-free graft according to any one of claims 1-2, wherein the serum is autologous, allogenic or heterologous and is optionally modified by adding at least one element.

9. Cell-free graft according to claim 3, wherein the serum is autologous, allogenic or heterologous and is optionally modified by adding at least one element.

10. Cell-free graft according to claim 1, wherein the serum is autologous, allogenic or heterologous and is optionally modified by adding at least one element.

11. Cell-free graft according to any one of claims 1-2, additionally comprising one or more elements selected from the group consisting of growth factors, differentiation factors, hormones, chemokines, cytokines, cellular adhesion molecules, chemotactic factors, enzymes, enzyme inhibitors, coenzymes, minerals, fats, lipids, saccharides, pharmaceutical substances, buffer substances, stabilizers, and vitamins.

12. Cell-free graft according to claim 3, additionally comprising one or more elements selected from the group consisting of growth factors, differentiation factors, hormones, chemokines, cytokines, cellular adhesion molecules, chemotactic factors, enzymes, enzyme inhibitors, coenzymes, minerals, fats, lipids, saccharides, pharmaceutical substances, buffer substances, stabilizers, and vitamins.

13. Cell-free graft according to claim 1, additionally comprising one or more elements selected from the group consisting of growth factors, differentiation factors, hormones, chemokines, cytokines, cellular adhesion molecules, chemotactic factors, enzymes, enzyme inhibitors, coenzymes, minerals, fats, lipids, saccharides, pharmaceutical substances, buffer substances, stabilizers, and vitamins.

14. Cell-free graft according to claim 8, additionally comprising one or more elements selected from the group consisting of growth factors, differentiation factors, hormones, chemokines, cytokines, cellular adhesion molecules, chemotactic factors, enzymes, enzyme inhibitors, coenzymes, minerals, fats, lipids, saccharides, pharmaceutical substances, buffer substances, stabilizers, and vitamins.

15. Cell-free graft according to claim 14, wherein the one or more elements are selected from the group consisting of insulin, PDGF, IGF, GMCSF, GDF5, GDF6, FGF, BMP2, BMP4, BMP7, IL8, SDF1-α and EGF and combinations thereof.

16. Cell-free graft according to claims 12, wherein the one or more elements are selected from the group consisting of insulin, PDGF, IGF, GMCSF, GDF5, GDF6, FGF, BMP2, BMP4, BMP7, IL8, SDF1-α and EGF and combinations thereof.

17. Cell-free graft according to claims 13, wherein the one or more elements are selected from the group consisting of insulin, PDGF, IGF, GMCSF, GDF5, GDF6, FGF, BMP2, BMP4, BMP7, IL8, SDF1-α and EGF and combinations thereof.

18. A method of producing a cell-free graft according to any one of claims 1-2, comprising placing the matrix and the gel in contact with the serum.

19. A method according to claim 18, wherein the contacting is effected by applying drops, softening, impregnation or soaking.

20. A method according to claim 19, wherein the gel is provided and is firstly incorporated in the matrix and/or applied to it, and then placed in contact with the serum.

21. A method according to claim 18, wherein the gel is provided and is firstly incorporated in the matrix and/or applied to it, and then placed in contact with the serum.

22. A method according to claim 21, further comprising drying the combination of gel and matrix as well as other optional constituents before or after contacting.

23. A method according to claim 20, further comprising drying the combination of gel and matrix as well as other optional constituents before or after contacting.

24. A method according to claim 22, wherein the graft is in a dried state, and the method further comprises reconstituting the graft from the dried state.

25. A method according to claim 23, wherein the graft is in a dried state, and the method further comprises reconstituting the graft from the dried state.

26. A method according to claim 22, wherein the contacting is effected by applying drops, softening, impregnation or soaking.

27. A method according to claim 19, further comprising drying the matrix as well as other constituents before or after contacting.

28. A method according to claim 18, further comprising drying the matrix as well as other constituents before or after contacting.

29. A method according to claim 27, wherein the graft is in a dried state, and the method further comprises reconstituting the graft from the dried state.

30. A method according to claim 28, wherein the graft is in a dried state, and the method further comprises reconstituting the graft from the dried state.

31. A process for regenerating tissue, comprising applying a cell-free graft according to any one of claims 1-2 to an area in need of treatment.

32. A process according to claim 31, wherein the tissue comprises mesenchymal tissue.

33. A process according to claim 32, wherein the mesenchymal tissue comprises cartilage and/or bone.

34. Cell-free graft according to claim 1, wherein the concentration of human serum present is sufficient in character and quantity so as to promote migration of cells into the graft during use of the graft for regenerating tissue.

35. Cell-free graft according to claim 15, wherein the concentration of human serum present is sufficient in character and quantity so as to promote migration of cells into the graft during use of the graft for regenerating tissue.

36. Cell-free graft according to claim 16, wherein the concentration of human serum present is sufficient in character and quantity so as to promote migration of cells into the graft during use of the graft for regenerating tissue.

37. Cell-free graft according to claim 17, wherein the concentration of human serum present is sufficient in character and quantity so as to promote migration of cells into the graft during use of the graft for regenerating tissue.

38. Cell-free graft according to claim 7, wherein the matrix comprises polyglycolic acid (PGA).

\* \* \* \* \*